(12) United States Patent
Tribelsky et al.

(10) Patent No.: US 6,555,011 B1
(45) Date of Patent: Apr. 29, 2003

(54) METHOD FOR DISINFECTING AND PURIFYING LIQUIDS AND GASSES

(75) Inventors: Zamir Tribelsky, Mevasseret Zion (IL); Michael Ende, Moshav Shoeva (IL)

(73) Assignee: Atlantium Ltd., Harey Yehuda (IL)

(*) Notice: Subject to any disclaimer, the term of this patent is extended or adjusted under 35 U.S.C. 154(b) by 0 days.

(21) Appl. No.: 09/959,249

(22) PCT Filed: Apr. 21, 2000

(86) PCT No.: PCT/IL00/00235
§ 371 (c)(1),
(2), (4) Date: Jan. 15, 2002

(87) PCT Pub. No.: WO00/64818
PCT Pub. Date: Nov. 2, 2000

(30) Foreign Application Priority Data

Apr. 23, 1999 (IL) .................................................. 129564

(51) Int. Cl.$^7$ ............................... C02F 1/30; C02F 1/48
(52) U.S. Cl. ........................ 210/748; 210/695; 210/222; 210/253; 210/255; 204/158.2; 204/554; 204/666; 422/20; 422/22; 422/186; 422/186.3; 422/187
(58) Field of Search .................... 210/748, 695, 210/222, 253, 255; 204/158.2, 554, 660, 666; 422/4, 20, 22, 168, 169, 186, 186.3, 187, 188

(56) References Cited

U.S. PATENT DOCUMENTS 5,130,031 A    7/1992   Johnston
5,727,108 A    3/1998   Hed
6,361,747 B1 * 3/2002   Dion et al.

FOREIGN PATENT DOCUMENTS

WO    97 37936    10/1997

OTHER PUBLICATIONS (1) C. E. Tyner, "Application of Solar Thermal Technology to the Destruction of Hazardous Wastes," Solar Energy Materials, NL, Elsevier Science Publishers B.V. Amsterdam, vol. 21, No. 2/03, Dec. 1, 1990, pp. 113–129.

* cited by examiner

*Primary Examiner*—Betsey Morrison Hoey
(74) *Attorney, Agent, or Firm*—Lowe Hauptman Gilman & Berner, LLP (57) ABSTRACT

The present invention relates to a method for disinfecting and purifying liquids and gasses comprising; a) passing said liquids or gasses through a reactor or a combination of reactors, having a truncated compounded concentrator geometry; and b) simultaneously delivering and concentrating diversified electromagnetic and acoustic energies into a specific predetermined inner space of said compounded concentrator reactor, forming a high energy density zone in said reactor or reactors over a predetermined period of time. The reactor according to the present invention is preferably a compounded parabolic concentrator or a compounded ellipsoidal concentrator. The electromagnetic energy delivered and concentrated into and inside the reactor can be of any range of the electromagnetic spectrum, such as ultraviolet, visible, infra-red, microwave etc., or combination thereof. The acoustic energy is of any suitable frequency. The radiation source delivering the electromagnetic radiation can be enclosed within the reactor or can be external to the reactor.

27 Claims, 8 Drawing Sheets

METHOD FOR DISINFECTING AND PURIFYING LIQUIDS AND GASSES

FIELD OF THE INVENTION

The present invention relates to a method for simultaneously disinfecting and purifying liquids and gasses. More specifically, the present invention relates to a method for disinfecting and purifying liquids and gasses by passing the liquids and/or gasses through a reactor of a compounded concentrator geometry, in particular, a compounded parabolic concentrator geometry, and simultaneously concentrating a plurality of launched and/or delivered, and/or diversified energies in motion into a specific predetermined inner space of the reactor to form a high energy density zone. The energies include acoustic and/or ultrasonic transient cavitation and electromagnetic energy from a variety of ranges of the electromagnetic spectrum (e.g., ultra-violet, visible, infra-red, microwave etc.).

The inner surface of the reactor is preferably covered by a thin layer of photo-catalyst such as titanium oxide and the inner surface is optionally grooved, or sub-wavelength synthesized to have a predetermined holographic grooving pattern to facilitate wavelength dependent reflection and/or refraction and/or diffraction or any combination thereof.

The present invention further relates to a concentrator for use in the above method (hereinafter called hydrodynamic Compounded Parabolic Concentrator, or HDCPC) and to arrays of such concentrators interconnected either serially or in parallel or in a combination thereof.

BACKGROUND OF THE INVENTION

Global need for efficient water disinfecting technologies is indisputable. Disinfecting technologies favor UV technology over the use of disinfecting chemicals, due to strict requirements for disinfectants and disinfecting by-products. UV light produced by conventional lamps is the principle means for generating UV energy with its non-residual effects creating no harmful compounding volumes (e.g. in comparison with chlorinating processes). These lamps are arranged in banks of lamps, often immersed in channels (or reactors) each hosting a large number of the lamps. The lamps, (such as mercury arc and vapor lamps, require expensive periodical replacement and maintenance. Current limitation imposed by the use of conventional lamp based reactors stem from their inability to combat colloidal deposits and/or hard water deposits efficiently. Further more, the use of protecting sleeves (e.g. quartz sleeves that are known for their ability to transmit deep UV of 200 nm to 320 nm) to ensure adequate protection for the lamps increases the cost further, often requiring allocation of additional resources as well as making it hard for designers, producers and/or end users to take advantage of an optical or acoustic concentrator orientation for reactors. The present invention is not so limited, and can be used for a wide variety of disinfecting, neutralizing, dissolving and deodorizing applications where liquids or gasses are to be treated.

The aim of the present invention is to provide a highly efficient method for disinfecting and purifying liquids and gasses by passing liquids and/or gasses through a compounded concentrator and simultaneously concentrating diversified electromagnetic and acoustic, ultrasonic (transient cavitation) energies into a high energy density and concentration zone where disinfecting or inactivation of DNA and RNA replication sequences (e.g. in noxious microorganisms) together with dissolving and neutralizing and deodorizing (e.g. organic and non organic compounds) of pollutants and polluted media take place.

An optically primitive form of non-imaging light concentrator, the light cone, has been used for many years [(Holter et al. (1962)]. During the years, the simple cone type optical concentrator has been evolved into complex structures that are more efficient, e.g. Compound Parabolic Concentrator (hereinafter called CPC), as disclosed in U.S. Pat. No. 5,727,108, or a Compounded Ellipsoidal Concentrator (hereinafter called CEC). Optical concentrators, such as CPC, have already demonstrated highly efficient harnessing and concentrating of solar energy collection, concentration, conversion and are well documented in fiber coupling applications.

Acoustic concentrators have been used for generations musical instruments such as the horn, flute, organ, and trumpet as well as other instruments. Acoustic geometrical concentration in buildings, temples, churches and other architectural structures has also been observed.

Cone shape interfaces for concentrating flows of liquids and gasses through particular conduit or chamber cross sections exist in many hydraulic and/or pneumatic system configurations.

SUMMARY OF THE INVENTION

The above mentioned optical and acoustic geometrical concentrators are used for separate purposes, i.e., for light concentration in optical concentrators and acoustic concentration and/or amplification in acoustic concentrators, but have not been used for both purposes simultaneously to treat liquids or gasses flowing through the concentrators. Furthermore, the above mentioned concentrators have never been used as hydrodynamic flow concentrators. More specifically, never before has a compounded concentrator been used at the same time to enhance liquid and gas flows and to concentrate electromagnetic and acoustic energies. The electromagnetic energy can be in any range of the electromagnetic spectrum, e.g. microwave, infrared, visible, ultraviolet etc., and the acoustic energy can be of any suitable frequency.

Surprisingly, it was found in the present invention, that using a compound concentrator as a concentrator or reactor in which both electromagnetic and acoustic energies interact while passing at the same time liquids and gasses through the reactor (having a single concentrator, and/or multi stage concentrator arrays) shaped reactor, enables disinfecting, and/or deodorizing and/or purification of the gasses and liquids with very high throughput efficiencies.

In the context of the present invention, "absorption" is the process by which substances in gaseous, liquid or solid form dissolve or mix with other substances (ASCE, 1985).

In the context of the present invention, "adsorption" is the adherence of gas molecules, ions, or molecules in a solution to the surface of solids (ASCEW, 1985).

In the context of the present invention, "adsorption isotherm" is a graphical representation of the relationship between the bulk activity of adsorbate and the amount adsorbed at a constant temperature (after Stumm and Morgan, 1981).

In the context of the present invention, "advection" is the process whereby solutes are transported by the bulk mass of flowing fluid (Freeze and Cherry, 1979).

In the context of the present invention, "air-space-ratio" is the ratio of (a) the volume of water that can be drained from saturated soil or rock under the action of gravity to (b) the total volume of voids (ASTM, 1980).

In the context of the present invention, "anisotropy" is the condition of having different properties in different directions (AGI, 1980).

In the context of the present invention, "anisotropic mass" is a mass having different properties in different directions at any given point (ASTM, 1980).

In the context of the present invention, "aquiclude" is a hydrogeologic unit which, although porous and capable of storing water, does not transmit water at rates sufficient to furnish an appreciable supply for a well or spring (after WMO, 1974).

In the context of the present invention, "aquifer" means a formation, a group of formations, or part of a formation that contains sufficient saturated permeable material to yield significant quantities of water to wells and springs (after Lohman et al., 1972) or a geologic formation, group of formations, or part of a formation capable of yielding a significant amount of ground water to wells or springs. Any saturated zone created by uranium or thorium recovery operations would not be considered an aquifer, unless the zone is or potentially is a) hydraulically interconnected to a natural aquifer, b) capable of discharge to surface water, or c) reasonably accessible because of migration beyond the vertical projection of the boundary of the land transferred for long-term government ownership and care (10 CFR Part 40 Appendix A).

In the context of the present invention, "aquifer system" is a body of permeable and poorly permeable material that functions regionally as a water-yielding unit; the body comprises two or more permeable beds separated at least locally by confining beds that impede ground water movement but do not greatly affect the regional hydraulic continuity of the system and includes both saturated and unsaturated parts of permeable material (after ASCE, 1985).

In the context of the present invention, "aquifer test" is a test to determine hydraulic properties of the aquifer involving the withdrawal of measured quantities of water from addition of water to a well and the measurement of resulting changes in head in the aquifer both during and after the period of discharge or additions (ASCE, 1985).

In the context of the present invention, "quifuge" means a hydrogeologic unit which has no interconnected openings and, hence, cannot store or transmit water (after WMO, 1974). A rock that contains no interconnected openings or interstices and neither stores nor transmits water (ASCE, 1985).

In the context of the present invention, "baseline monitoring" means the establishment and operation of a designed surveillance system for continuous or periodic measurements and recording of existing and changing conditions that will be compared with future observations (after NRC, 1982).

In the context of the present invention, "breakthrough curve" is a plot of relative concentration verses times, where relative concentration is defined as C/Co where C is the concentration at a point in the ground water flow domain, and Co is the source concentration.

In the context of the present invention, "UV radiation" is optical radiation of from about 200 nm–400 nm (e.g. are used to inactivate noxious microorganisms).

In the context of the present invention, "visible radiation" is optical illumination of from 400 nm to 700 nm.

In the context of the present invention, "PDMS" means polydimethilsiloxan which is used in elements of devices for use in the method of the present invention (e.g. to form elastic conduit and chambers).

In the context of the present invention, "resolved" means synchronized to an accurate clock or time track (such as synchronizing laser, ultrasound probe, air flow, water flow, timed spectroscopy, oxygen mixing & melting time, radicals production and sustain time, pressure levels, peak power, pulse repetition rate, intensity, wavelength).

The present invention provides a method for disinfecting and purifying liquids and gasses comprising; a) passing the liquids or gasses through a reactor, or a combination of reactors, having a truncated compounded concentrator geometry; and b) simultaneously delivering and concentrating diversified electromagnetic and acoustic energies into a specific predetermined inner space of the compounded concentrator reactor, to form a high energy density zone in the reactor or reactors over a predetermined period of time.

The reactor according to the present invention is preferably a compounded parabolic concentrator or a compounded ellipsoidal concentrator.

According to the present invention, the inner surface of the reactor is coated with a thin layer of photocatalyst such as $TiO_2$.

The electromagnetic energy delivered and concentrated into and inside the reactor can be of any range of the electromagnetic spectrum, such as ultra-violet, visible, infrared, microwave etc., or any combination thereof.

The acoustic energy is of any suitable frequency.

The radiation source or sources delivering the electromagnetic radiation can be enclosed within the reactor or can be external to the reactor or both. The radiation source/s can be a laser, e.g. either a continuous wave laser or a pulsed laser.

In a preferred embodiment of the present invention, the radiation unit having a high intensity source of light is a flash lamp having a high repetition rate of from about 1 Hz to about 50 kHz, and a high peak power of from about 1 mJ to about 50 J.

The present invention further provides a method wherein the liquids and gasses are passed through an array of at least two compounded parabolic reactors connected serially or in parallel or in a combination thereof.

The present invention further provides a device for use in the method wherein the device is a hollow truncated compounded concentrator having a wider inlet and a narrow outlet to allow gasses and liquids to flow through and the concentrator has a specific predetermined optical concentrating geometry capable of concentrating light to form a high density energy zone therein. The concentrator's inner shape can be a compound parabolic or ellipsoidal concentrator geometry or any other compounded concentrator geometry.

The inner surface of the device can be coated with photocatalyst, such as $TiO_2$ (titanium oxide). The inner surface can be coated by plasma spattering coating the photocatalyst at a thickness of from about 0.8 micron to about 1000 micron and can be applied on a substrate layer of $SiO_2$ of a thickness of from 0.8 micron to about 1500 micron, thus forming a predetermined refractive index.

The refractive index of the coated material can be lower than the refractive index of the liquids or gasses which flow in the reactor.

The coated layers can have a plurality of grooves that are arranged in parallel or in a grid configuration, wherein the distance between two successive grooves is less than the wavelength of light incident upon the grooves.

It is within the scope of the present invention the reactor is a part of a reverse osmosis system or a filtration system.

The present invention provides a novel methodology wherein a plurality of energies interact in space and time to produce a high energy density zone, which is especially beneficial for disinfecting, dissolving and neutralizing pollutants in liquids and gasses (such as water & air). Furthermore, the method of the present invention facilitates continuous interaction of diversity of energies to form a high energy density zone.

Such a zone is particularly useful for:

(a) Disinfecting liquids and gasses;

(b) Dissolving organic and/or non-organic compounds (e.g. such as polluting compounds); and (c) Normalizing and/or Neutralizing liquids and gasses with a maximized perpetual output throughout.

BRIEF DESCRIPTION OF THE DRAWINGS

The present invention is illustrated by way of example, and not by limitation, in the figures of the accompanying drawings, wherein elements having the same reference numeral designations represent like elements throughout and wherein.

DETAILED DESCRIPTION OF THE INVENTION

The present invention provides a novel and unobvious method for (a) harnessing diversity of energies into a modular compounded concentrator geometry, (b) compounding and (c) catalytically and/or interactively impacting (d) a predetermined amount of diversified energies produced simultaneously within the geometry through which liquids or gasses containing pollutants or noxious species flow, so that the pollutants become more innocuous as a result of (e) time resolved synchronized impact diversity of wavefronts for the purpose of forming a maximized energy density of all wavefronts in a (predetermined) space or zone which zone is useful for disinfecting, dissolving and/or neutralizing or inactivating the pollutants in the liquids or gasses over a predetermined period of time. Furthermore, the Failure Modes Evaluation and Criticality Assessment (FME/CA) surpass. Limitations imposed by conventional systems using $TiO_2$ optical catalyst where catalyst triggering relies heavily on the source of light (e.g. light must be present if catalyst triggering is to occur) are overcome. The present invention utilizes harnessing and concentrating of both laser light (190 nm to about 315 nm) and Ultrasound Transient Cavitation (21–180 Khz) which produces sonoluminecense in the region of from 212 nm to about 511 nm. Thus, in the present invention the optical catalyst is triggered in more than one way. increasing substantially the safety margins of devices used in the method of the present invention. The present invention provides a novel methodology for concentrating different energies into a specific predetermined inner space, in or through which liquids and/or gasses flow that has an uniform high energy density zone for the purpose of inactivation of DNA and RNA replication sequences in noxious microorganisms and/or dissolving and neutralizing organic, non-organic and Disinfectant By-Products (DBPs). Furthermore, the present invention composedly harnesses a compounded plurality of energy wavefronts together (e.g. simultaneously) in a single (e.g. HDCPC) reactor for the purpose of disinfecting by creating a uniform dimensionally distributed high energy density zone within a conduit or chamber (e.g. a reactor).

The present invention further provides a method and device for disinfecting, catalytically dissolving or neutralizing biological, organic and non organic pollutants and polluted media by interactively resolving the interoperability of optical peak power, acoustic transient cavitation and laser triggering of a subsurfaced optical catalyst.

The present invention presents a novel methodology wherein devices for use in the above method can be integrate into an existing pressure vessel (filtration systems) or can be added before or after or be integral to the systems operating in the molecular and/or particulate filtration levels or any combination thereof. Furthermore, the present invention provides benefits, increasing the safety margins of existing filtration and purification systems (e.g. such as reverse osmosis, super filtration, membrane systems and larger particulate filtration systems).

PREFERRED EMBODIMENTS OF THE PRESENT INVENTION

According to a preferred embodiment of the method of the present invention, a plurality of CPCs that are arranged serially to increase efficiencies and/or in parallel to increase throughput efficiencies form HDCPC arrays in which each HDCPC represents a concentration stage (e.g. $1^{st}$ stage, $2^{nd}$ stage, $3^{rd}$ stage and so forth). Thus, enhanced multi-stage concentrator arrays, in which a water inlet leads to the input of the $1^{st}$ stage and a water outlet leads to the last concentration stage, or a parallel arrangement driven by at least one remotely connected laser or a dedicated laser source for each module are provided.

According to a preferred embodiment of the present invention, a plurality of HDCPCs that are arranged to form a plane, or a flat screen of CPCs wherein most of their wider inputs face upwards or downwards or positioned at a predetermined angle or any combination thereof are provided.

According to a novel environment friendly embodiment of the present invention, a central light source (such as a solid state diode pumped pulse laser) provides sufficient light energy for at least one concentration stage comprising a Hydro-dynamic-Compound-Parabolic Concentrator. Furthermore, in an environment friendly preferred embodiment of the present invention, the inner walls of the HDCPC are Holographically grooved using an E. beam or a laser beam for creating a sub-wavelength surface having an adequate refractive index for steering and/or manipulating rays of light (e.g. laser pulses), and the manipulation forms a high energy density zone, especially beneficial for disinfecting, dissolving and/or neutralizing noxious species.

According to a novel environment friendly embodiment of the present invention, a serial arrangement of CPCs is used to create a multi-stage concentrator having a sufficient length for irradiation at each concentration stage, and a sequentialoperation mode to maximize the interaction therein of photo-catalysts and laser radiation (e.g. production of free radicals and limiting and/or neutralizing the radicals). A further novel environment friendly embodiment of the present invention provides a parallel arrangement of series of CPCs instead of/or in combination with the above serial arrangements, or any combination thereof.

A beneficial embodiment of the present invention provides at least one CPC having a metallic body with an inner surface plasma spattered and/or coated with a layer of $SiO_2$, wherein the $SiO_2$ substrate layer is coated witj $TiO_2$ or a photo-catalyst. Furthermore, according to a novel aspect of the present invention, the coated material has a predetermined refractive index for enhancing reflection and/or triggering of photo-catalyst (e.g. in the HDCPC reactor).

In a preferred embodiment of the present invention, there is provided a concentrator reactor wherein liquids or gasses passing through the reactor are disinfected in a high energy density zone formed therein. Furthermore, the present invention provides the ability to dissolve and/or neutralize pollutants and/or noxious microorganisms.

In a useful environment friendly embodiment of the present invention, parts of the CPCs are coated to reflect wavelengths of from about 190 nm to about 399 nm and other parts or portion are coated to absorb wavelengths of from about 199 nm to about 400 nm, ensuring the formation of a high energy density zone in predetermined portions of the HDCPC's inner surface which has been coated with photo-catalyst.

In a preferred embodiment of the present invention, each CPC is attached or connected or integral to at least one additional CPC, and groups of CPCs are interconnected dimensionally or in a frame, or any combination thereof.

In a preferred embodiment of the present invention, the inner surface of at least one CPC is curved or twisted or grooved to increase its contact surface with the liquids or gasses which flow therein. Furthermore, such grooving or curving is done on the final layer in a multi-layer coating formed by plasma sputtering, or vapor deposition or surfacing, or any combination thereof.

The method of the present invention can be used in a wide range of diversified and environmentally beneficial (e.g. disinfecting, and/or dissolving and/or neutralizing) applications that require each element of the method of the present invention to operate separately or in unison and/or synchronously with additional elements selected from (1) monochromatic pulsed laser (or filtered lamp) optical energy, (2) ultrasound transient cavitations, (3) microwaves, (4) air bubbles for oxygen input (e.g. to $1^{st}$ stage) in waste water and/or liquids or gasses, (5) sonoluminecence, (6) ozone produced in situ for mild residual neutralization and/or oxidation effects, (7) polychromatic Continuos Wave (CW) (e.g. UV optical energy), (8) enriched air bubbles (e.g. added radicals by placing photocatalyst earlier in the chain taking advantage of the superior transmission of air and its 21% available free oxygen), or any combination thereof.

In a preferred embodiment of the present invention, a CPC can be of a size of from about several centimeters (e.g. to have flow through capacity of several liters per minutes or seconds) to about several hundred meters (to accommodate a large volume of standing or temporarily stored liquids or gases). Such large CPCs can be beneficial for environmental applications wherein air is bubbled into the bottom center of a pool or pond and light is delivered to the pond/pool via individual waveguides and/or integrated arms or from a separated concentrator and/or concentrator arrays.

In a preferred embodiment of the present invention, modules containing each at least one HDCPC are connected in serial and/or parallel to form platforms or stations of modules. Such stations and platforms are especially beneficial, providing additional exposure time for the liquids and gases therein (e.g. to UV light and/or ultrasound or more than 26 KHz), production of free radicals and sufficient time for the radicals to work efficiently, additional spaces for ultrasound waves to clean, additional irradiation points or inputs for ensuring that the innocuous outputs contain no radicals (e.g. by irradiating UV at the outlet stage of the system).

In a preferred embodiment of the present invention, a photocatalyst insert is used. The insert provides a convenient means which can easily be cleaned (e.g. by back-flashing). Furthermore, by using a photocatalyst insert, the manufacturing and production costs of devices for use in the method of the present invention are substantially reduced. By using photocatalyst inserts, producers and/or end users can scale up or down their systems (e.g. reactors) without the need to use expensive coating procedures. End users as well as producers can simply scale up their system hardware and select appropriate photo-catalyst inserts to suit their specific sized.

Thus, the use of photo-catalyst inserts will increase the quality and the reaction rate of the photocatalyst.

In a preferred embodiment of the present invention, at least one HDCPC contains a turbine therein and the turbine is coated with or made of photo-catalysts. Rotation of the turbine within the reactor enhances the reaction rate of the photocatalyst therein (e.g. in the reactor).

Figure 1:
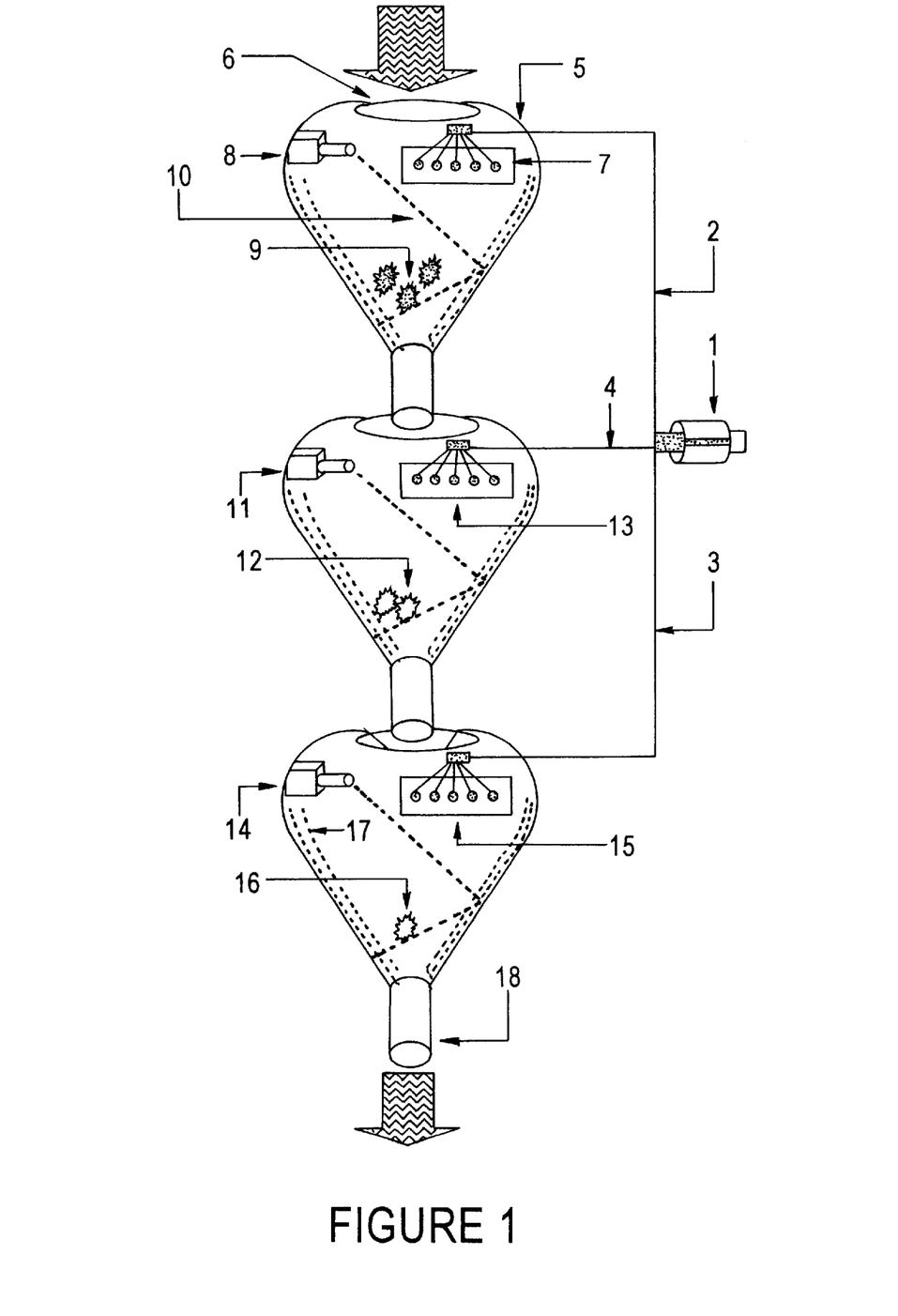
FIG. 1 is a schematic view of an array of serially connected HDCPCs according to the present invention.

FIG. 1 illustrates a device according to the invention that has Truncated-Hydro-Dynamic-Compound-Parabolic-Concentrator (THDCPC) reactor geometry with a diffractive Sub-Wavelength-inner Surface (SWS) integrated with a laser triggered Opto-aerobic-flow-resolved Optical Catalyst (such as $TiO_2$). The present invention includes (a) HD/CPC conduit geometry having input and output openings, (b) Ultrasonic Transient String Cavitation, (c) hydrodynamic interface, (d) thermodynamic interface, and (e) in-situ production of mild residual ozone, which are extended to simultaneously operate (time resolved, or locked) for synchronous interconnectivity and harmonious interoperability to manipulate the collective interactive impact of a diversified variety of energies and their associated wavefronts in a predetermined space over a predetermined period of time.

In a preferred embodiment of the present invention, a plurality of HDCPCs are arranged sequentially into modules, and each module is connected to at least one additional module in a predetermined sequential order (e.g. in a straight line arrangement, and/or parallel arrangement, and/or serial arrangements and/or any combination thereof). Furthermore, the present invention provides a novel methodology wherein the output absorber exit is seamlessly interconnected to the next entrance aperture of a predetermined HDCPC. This arrangement for multi stage concentration arrays is especially beneficial for disinfecting, dissolving, neutralizing and deodorizing liquids and gasses in water purification applications with enhanced distribution of appropriate dose, and/or dose delivery that facilitates high throughput efficiency while maintaining simplicity and modularity for economical interoperability between end users and producers.

In a preferred embodiment of the present invention, a parallel arrangement of HDCPCs is interconnected to a serial arrangement. Furthermore, any number of arrangements can be (inter) connected together to form modules. Modules can be grouped, connected or stacked to meet the growing demands for modular solutions and the ability to quickly respond to changing throughput needs of a predetermined application.

In a preferred embodiment of the present invention, the output absorber of a predetermined HDCPC is the input of an additional HDCPC connected thereto. Furthermore, a number of HDCPCs can be connected into a single HDCPC and/or merged to form a single unit (or module) or an array of units. By using a modular architecture, the present invention surpasses limitations imposed by conventional CW UV lamp based reactors.

In a preferred embodiment of the present invention, a plurality of HDCPCs are connected and/or integrated together serially or in parallel to form a network of interconnected HDCPCs with a plurality of high energy density zones, that is especially beneficial for disinfecting, dissolving, neutralizing and deodorizing liquids and gasses. Furthermore, the method of the present invention, by using at least one stage of concentration, provides sufficient time for the free radicals (produced by the photo-catalysts inside each HDCPC) to dissolve, neutralize and be neutralized by UV irradiation at the final stage (e.g. at the output).

In a preferred embodiment of the present invention, a preliminary oxygen melting reactor is included prior to the laser and/or photo-catalyst stage (reactor) for the purpose of increasing the amount of melted oxygen in the water and so also increasing the reaction rate of the photo-catalyst (e.g. in the respective stage/reactor). Furthermore, the melting stage can utilize the heat from the laser (e.g. by cooling the laser by the water or air passing through different stages), or take advantage of Infra Red radiation from the laser (e.g. prior to frequency doubling), or be enhanced by transmitting microwave energy into the liquids or gasses (e.g. water and/or air), or include mixing air with water (for melting oxygen into water), or include mixing air with water with the aid of ultrasound transient or stable cavitation, or any combination thereof.

In a preferred embodiment of the present invention, optical peak power, and/or ultrasound transient cavitation, and/or flow resolved light (such as from about 170 nm to about 364 nm) triggered photo-catalyst, and or sonoluminecence, and or oxygen melting, dissolving or mixing (e.g. into liquids and gasses) occur together synchronously and/or sequentially, and/or in unison for the purpose of disinfecting, and/or dissolving, and/or neutralizing, and/or deodorizing noxious species (e.g. such as bacteria or viruses and/or cysts) and/or pollutants in liquids and gasses.

In a preferred embodiment of the present invention, a series of HDCPCs are connected in straight and/or curved lines and the entrance of the $1^{st}$ concentrator (e.g. in at least one line of HDCPCs) receives a coherent laser beam from a high intensity source of light. The light includes pulsed or continuous waves and/or the light is invisible with a wavelength of from about 170 nm to about 400 nm or visible with a wavelength of from 401 nm to about 700 nm to form in each HDCPC a high energy density zone, that is especially useful for disinfecting, dissolving, and/or neutralizing noxious species and pollutants.

In a preferred embodiment of the present invention, a solid state diode pumped laser having a high repetition rate and a high peak power is operating at 3 wavelengths (1) from about 1064 to about 2400 nm, and (2) from about 532 to about 1063 nm, and (3) from about 266 nm to about 531 nm. The wavelengths are utilized individually and/or collectively for the purpose of disinfecting, dissolving, neutralizing and deodorizing liquids and gasses. Furthermore, the present invention provides a novel methodology wherein each wavelength is harnessed and distributed and/or delivered to a predetermined location within the system architecture so it can be used to enhance the overall process of disinfecting.

In a preferred embodiment of the present invention, the Infra Red portion of laser radiation is delivered by wave-guides and/or within an integrated arm to a pre-reactor and/or module dedicated to the melting and/or mixing of oxygen into the water or gas (in the pre-reactor). Furthermore, the laser cooling system (air to water, water to water, air to air, or any combination thereof) could be connected in order to increase the temperature at a specific location before, between, or after water inlets or outlets.

In a preferred embodiment of the present invention, the liquids or gasses passing through the reactor (HDCPC) are enriched and/or mixed with and/or toned with dissolved oxygen prior to or during, or after passing through any main HDCPC unit or module (e.g. a reactor, and/or a reactor array or a chain of reactors, or any combination thereof).

In a preferred embodiment of the present invention, a continuous wave laser beam (CW) is launched through the input of serially interconnected HDCPC modules. Furthermore, the serial arrangement of HDCPCs facilitates continuous concentration of the reflected laser beam throughout each HDCPC individually to create a sequence of high energy density zones throughout the system (e.g. throughout the HDCPC array or interconnected reactor arrays). Thus, the present invention advantageously overcomes limitations imposed by conventional lamp and laser based reactors. More specifically, the present invention provides sufficient time for the free radicals produced by the photo-catalyst (and oxygen) which is constantly triggered by the laser (in the HDCPC reactor and/or arrays of reactors). Furthermore, the present invention facilitates the formation of a modular network of reactors which, when connected, and/or inter-operating together (e.g. resolved, and/or synchronized together), provides an enhanced efficiency of inactivation of (disinfecting, dissolving, and/or neutralizing). More specifically, the present invention, by utilizing (a) multi stage optical concentrators (e.g. HDCPCs), and (b) multi stage exposure chambers and/or reactors connected to form (c) a network, allows producers and/or end users (as well as liquid and/or gas system managers) to turn noxious species present in the liquids and/or gasses (which flow through a predetermined reactor, HDCPC module or HDCPC array or network of arrays) into more innocuous substances that are acceptable and/or consumable by humans, animals or plants. Furthermore, such processes (a, b, c,) are performed faster, more efficiently and more economically then any other known method in the field.

In a novel environment friendly embodiment of the present invention, a single module of HDCPCs contains a plurality of individually connected smaller modules. Furthermore, the individual modules (and/or reactors) may include the following types: photo-catalyst type, wave guide type, pulse exposure type, continuous wave (CW) type, Quasi CW type, suspension type, oxygen melting and/or mixing type, heating type, cooling type, temperature and/or flow exchange type, visible illumination type, IR irradiation type, UVA, UVB, UVC irradiation types, polychromatic type, monochromatic types, flash lamp types, diode types, laser types, aerobic and/or non-aerobic types, integral filtration types.

The following are aspects and applications of the present invention:

Optical (E.M.R);

Acoustic (ultrasonic) transient/stable Cavitation;

Hydrodynamic flow of liquids and gasses (e.g. such as aqueous media);

Laser triggered optical catalyst (e.g. pneumatically and aerobically (oxygen enhanced);

Microwave generation means or magnetron; and

Medical Resolved Equalizer/Resolver.

A preferred embodiment according to the present invention wherein a catalytic disinfecting (medical) instruments holder is using the method of the present invention. This embodiment of the present invention provide an essential tool in which safe medical treatment and procedures could be provided substantially faster, safer reducing the dependency on expensive energy and/or time consuming processes (e.g. autoclaving, or use of Oxygen water and other solvents and toxic compounds) A doctor, surgeon, bio-technologist, dentist, agronomic specialist, researchers, teachers and multi-discipline practitioners could place instruments inside the holder such instruments could include; blades, laser components, mirrors, drilling accessories, ultrasound probes, sampling tools, needles and/or medical and/or industrial syringes.

A preferred embodiment of the present invention wherein the disinfecting catalytic-medical-instrument-holder is made out of transparent sheath and/or layer of polymeric combinations (e.g. PDMs) wherein said sheath of polymer is sufficiently transparent and/or transitively positioned in a predetermined angle within the path of at least one incident light beam or pulse. Further more, such sheath of polymers could be coated (plasma spattering, CVDs variety of coating) in order to alter their optical and/or mechanical properties (e.g. such as refractive index, their module of flexibility as well as their texture, absorption, transmission, reflection, diffraction,). The elasticity aspect is of vital important enabling devices according to the method of the present invention to whistand strong impact and to offer solution in field use.

DETAILED DESCRIPTION OF THE FIGURES

The present invention will be further described and illustrated by the following figures:

FIG. 1 illustrates a schematic view of serially connected HDCPCs array according to the method of the present invention. An array of sequentially or serially interconnected HDCPCs is shown comprising: (1) A remote radiation unit having high intensity source of light powered by existing electrical infrastructure or solar panels, converter and/or battery, not shown (2) a wave-guide aligned between the radiation unit and the upper-most CPC ($1^{st}$ stage concentration) (3) An electrical guide (could be conductive coating on wave guide sheathing or internally bundled conductive (electrical and/or optical) member, (4) A bundle of optical and/or electrically conductive members is shown reaching to the $2^{nd}$ CPC in the chain (e.g. $2^{nd}$ stage concentration) wherein the liquids and/or gasses flow therein or throughout. Number (5) outline the body of the first CPC in the chain. Number (6) indicates the inlet (e.g. water & air, e.g. liquids or gasses), this point is illustrated for clarity showing a cylindrical pipe like system input) indicating the system input (e.g. reactor array input, HDCPCs module). Number (7) illustrate an input array from the bundle, these input represent points from which light from about 190 nm to about 399 nm is projected into the HDCPC enclosure and/or reactor body (e.g. $1^{st}$ stage concentration). An integral ultrasound probe is illustrates as number (8) with a doted line (10) cutting across the cross section of the $1^{st}$ stage HDCPC architecture (e.g. reactor 1 in the chain of only 3 illustrated HDCPC concentration/filtration stages) illustrating the (echoing) acoustic reflection of the stream of transient cavitation. From about 26999 Hz (26.9 kHz) to about 51000 Hz (51 kHz) Number (9) represent a group of bacteria clusters (e.g. such as E.coli wild type strain K 12, and/or other noxious species present in liquids and/or gasses). Number (11) represent second ultrasound probe which project acoustic transient cavitation from about 26 kHz to about 1.5 MHz within the $2^{nd}$ HDCPC stage reactor. Number (12) Represent remaining bacteria cluster group from stage 1). Number (13) represent input area of the waveguides into the $2^{nd}$ stage reactor (e.g. HDCPC), being shown for clarity as receiving an individual bundle feed from a pulsed light source having a high intensity, high peak power (e.g. high repetition rate, the delivered light form about 210 nm to about 370 nm is delivered along with electrical energy (e.g. in individual strands within the bundle), said bundle is illustrated as delivering optical, electrical, time, spectroscopy, temperature, magnetic fields BI-directional sensing data relevant to operation of each individual HDCPC unit, module, or array/s (not shown). Number (14) represent $3^{rd}$ ultrasound probe operating from about 10 Hz to about 110 Khz aiding, preventing and removing colloidal and/or hard water deposits (from the liquids and gasses which flow therein) (as in previous stage) therein (in each respective individual HDCPC stage and/or module, and/or array of HDCPCs reactors. Number (15) represent $3^{rd}$ input from individual bundle feed, this compounded optical input is especially designated and delivered according to species specific calibration standards to neutralize remaining free radicals and/or DBPs (e.g. Disinfectant By Products) from previous stages. Number (16) illustrates an inactivated bacteria cluster (e.g. disinfected) on its way to output the third stage (e.g. water or air outlet). Number (17) illustrates a two layers plasma spattered coating comprising SIO2 $1^{st}$ substrate smoothed and impact resistant having high adhesive power and a predetermined refractive index from about 1.00 to about 6.1, forming sufficient refractive index profile with additional layers of TIO2 photo-catalyst plasma spattered from a thickness of about 0.8 micron to about 1000 micron (each layer) forming wave guide type concentrator geometry with enhance transmission throughout. Number (18) represent the output of the system (e.g. such as water and/or air outlet).

Figure 2:
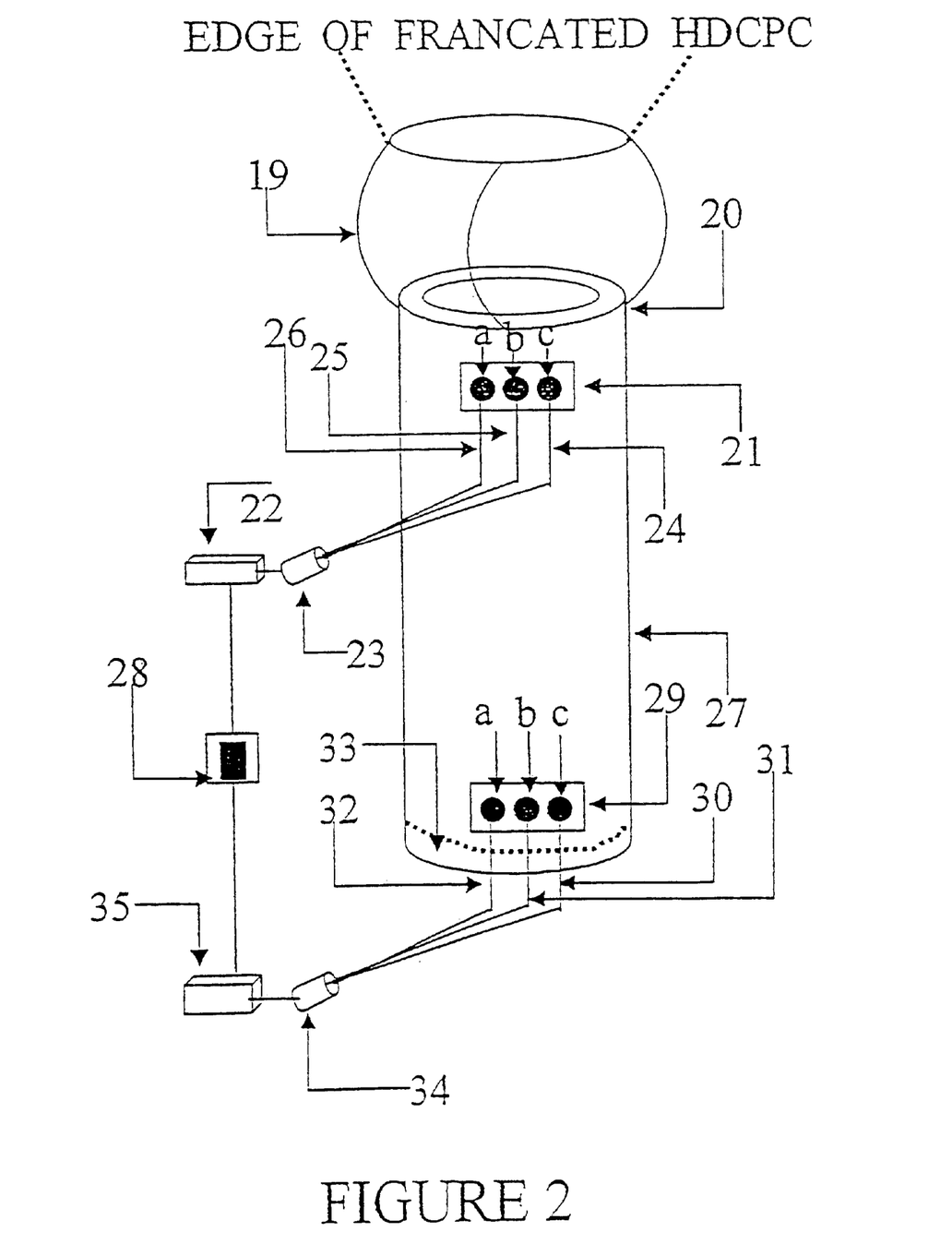
FIG. 2 is a schematic view of the waveguide portion of an element in a reactor which is a HDCPC waveguide type device according to the present invention.

FIG. 2 illustrates a schematic view of the waveguide portion of an element in a reactor, this HDCPC waveguide type device according to the present invention is shown comprising (19) truncated output of the last HDCPC module, or array interconnected by a quick coupling point (20) to a dielectric hollow waveguide (27) (HDCPC fin type) extending to form a single element of a reactor or module enclosure (not shown). (21, a, b, c,) Illustrates optical inputs into the dielectric waveguide projecting light from about 190 nm to about 2400 nm arriving from external radiation unit having a high intensity source of light delivered through waveguides and/or bundles of waveguides into the extended HDCPC waveguide fine, extending from about 1 micron to about several meters in length from the edge of the HDCPC, (e.g. see 19). (220 represent an individual controller for a dedicated high repetition rate, high peak power pulsed laser (23). (24), (25), (26), represent individual bundle feeds, delivering optical as well as electrical energies into the waveguide portion of the element. The body of the waveguide portion of the reactor element is shown (27), wherein (28) represent a single controller, which control both (22), and (34, a flash). (29, a, b, c,) represent additional optical input/output positioned at the far end of the waveguide portion of the reactor element. These additional I/Os provides refreshing optical input (e.g. further increasing the flux density in the wave guide portion of the element) or they could be used to take an optical sampling point for measurements and/or diagnostics. (30), (31), (32), represent individual bundle feeds reaching from a remotely positioned high intensity pulsed flush lamp (34) from about 210 nm to about 400 nm with its individual controller unit illustrated for clarity by (35). This figure illustrate an element (e.g. the waveguide portion) from the reactor and/or module, waveguide portions could be grouped or interconnected serially and/or in parallel or in any combination thereof to form modules of HDCPCs, according to the method of the present invention.

Figure 3:
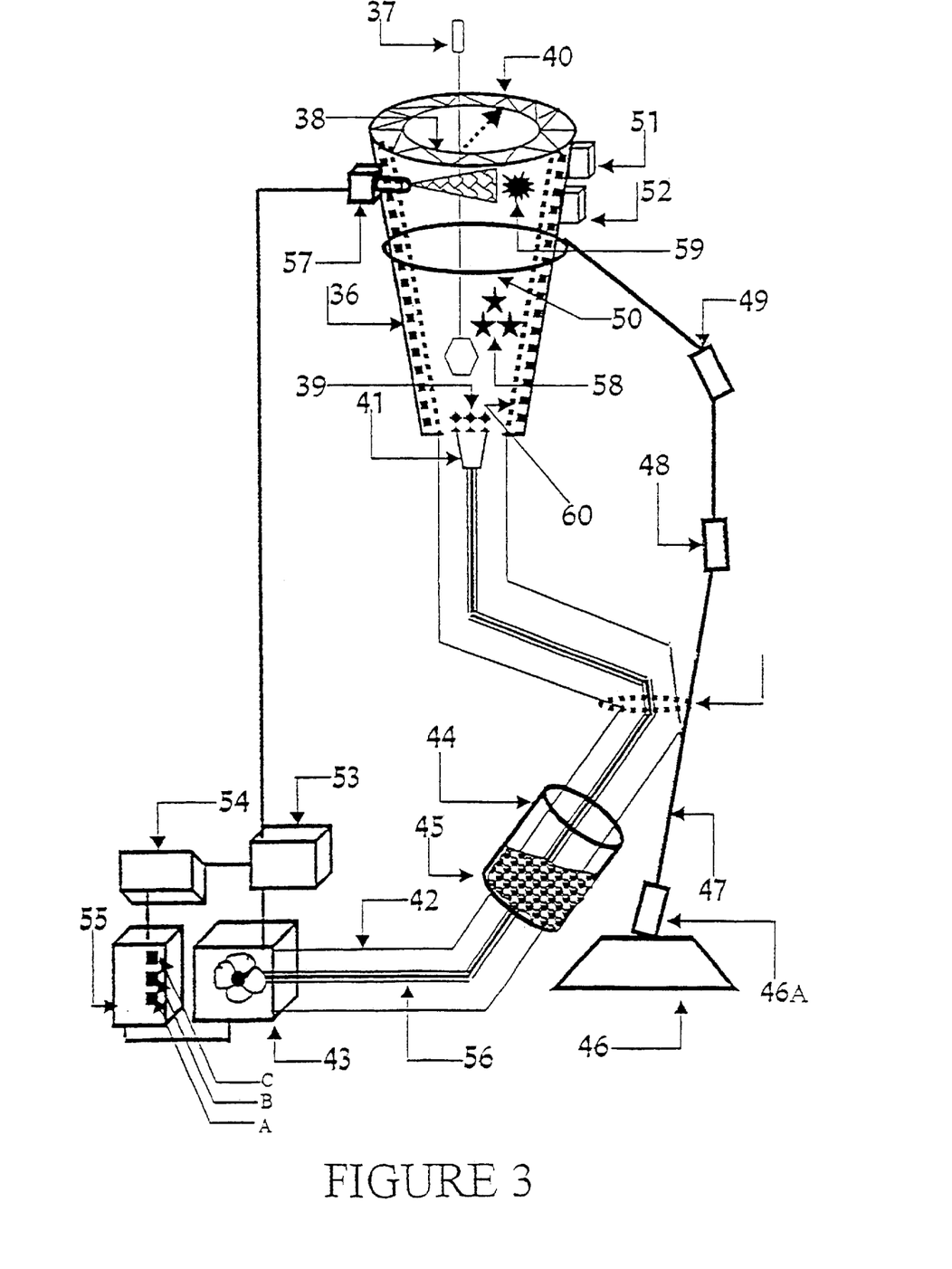
FIG. 3 is a panoramic exploded view of a medical instrument holder/resolver according to the present invention.

FIG. 3 illustrates a panoramic exploded view of a device according to the method of the present invention, a medical instrument holder Resolver is shown comprising HDCPC and/or conic conduit or chamber (36). An opto-aerobically turbidity and mixing spring expanded with sub-wavelength grooving and larger grooving to increase its surface interaction (e.g. air contains 21% of free available oxygen, increasing air flow will increase catalytic co-efficiencies). A Truncated Compound Parabolic Concentrator body (shown in this illustration in its preliminary conic profile) (TCPC) (36) with (38) wider concentration acceptance angle facing upwardly with sub-wavelength surfaced inner profile, Holographically grooved for wavelength signature controlling and manipulating optical interaction from about 200 nm to about 372 nm therein (e.g. in the TCPC). A touch-sensitive triggering absorber (39) is illustrated for clarity at the narrower accepted angle being both (a) reflective to the appropriate wavelength therein (in the HDCPC), (b) physically holding or supporting the instruments and/or elements therein. A surgical instrument (37) is shown inside the conical (e.g. concentrator reactor body with an adjustable aerobic sub-surfaced Holographically grooved automated iris (38) lead shutter, having wavelength specific, reflective, inwardly facing surface and (40) soft elastic contact edges for instrument protection, said iris is shown (e.g. triggered) closing (or opening) automatically around the surgical instrument protecting eyes of surrounding observers while maximizing catalytic disinfecting co-efficiencies therein by the production of free radicals from the photocatalyst (e.g. in the THDCPC body). Light enters the THDCPC body from and/or through the surface edges of a difractive optical element (41b) dimensionally (holographic and/or diffusive matching to the surface curvature of said spring and/or THDCPC body (36) inner profile for maximum interoperability and/or reaction rate throughput efficiency throughout. A dielectric air pipe is illustrated (42) with one end (41a) entering the body of the concentrator from the center output absorber (41, at the bottom of figure), and other end (43) terminates at an air pumping and/or sucking distant point. A water chamber (44) and/or conduit is illustrated for clarity with partially filled with liquid (such as water) illustrated by (45). The stand of the instrument holder/Resolver is illustrated by (46), (46, a), (47), (48), (49) as having telescopic or variable length supporting means or arms. A supporting ring (50) is illustrated for clarity holding the concentrator body (e.g. the conical reactor) (51), and (52) represent sensing means to sense and identify the inserted instrument. (53) Represent a driver and controller for the ultrasound transient cavitation probe (57) illustrated at the upper left side of the figure. (54) Represent a synchronizer or a Resolver unit with integral timer (not shown). (55) Represent the system main controller with integral triggering inputs illustrated for clarity by (a), (b), (c).

Figure 4:
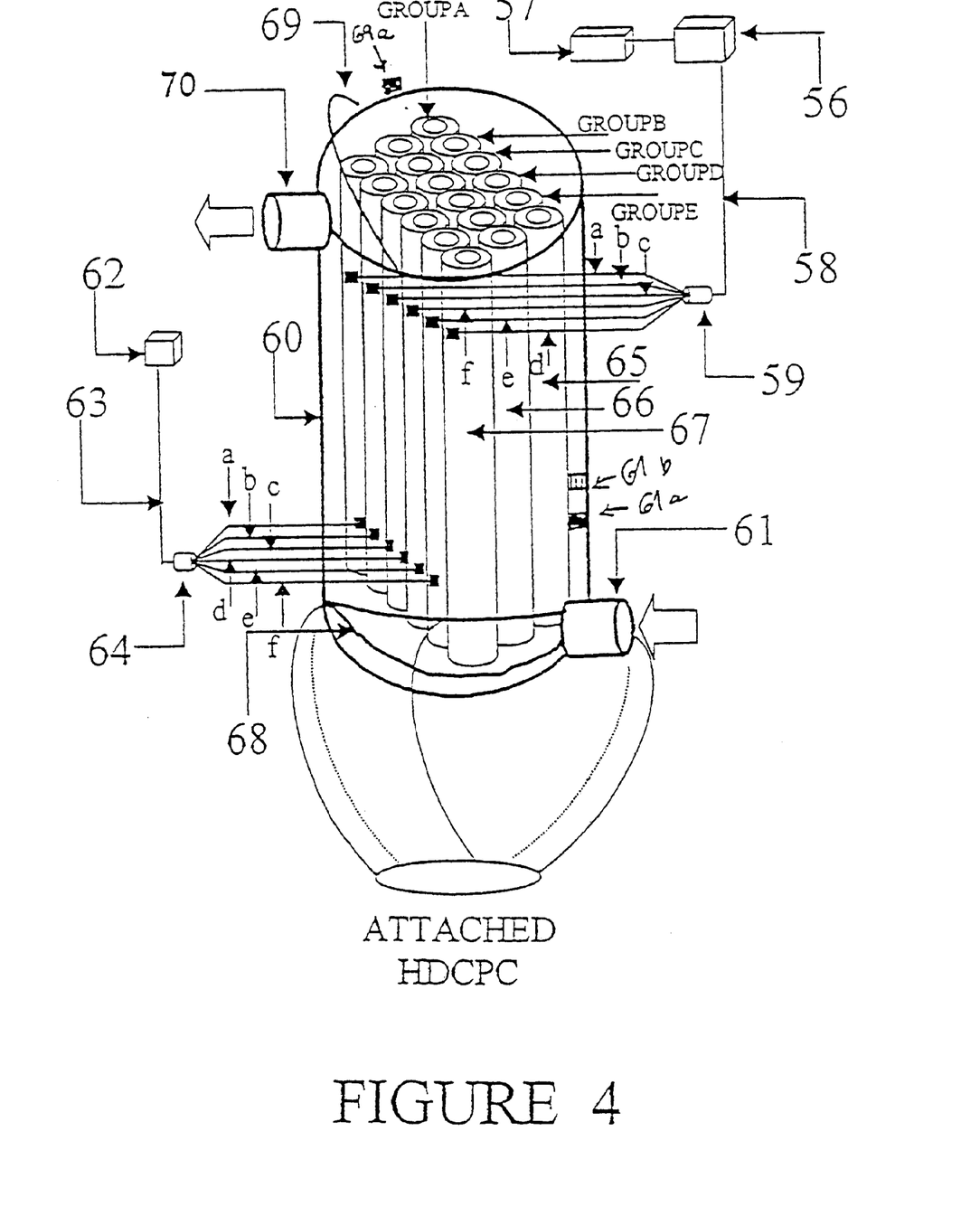
FIG. 4 is a panoramic explosion view of an HDCPC module according to the present invention.

FIG. 4 illustrates a panoramic explosion view of an HDCPC module according to the present invention. A HDCPC module is shown comprising a central controller (57), which electrically drives a radiation unit having a high intensity source of UV light from about 190 nm to about 400 nm. The light is delivered via a bundle of waveguides (58), (not shown), (59) represent said wave guides common-end-termination which splits into (a), (b), (c), (d), (e), and (f), each representing individual optical input into the respective HDCPC waveguide-portions (e.g. within the module) enclosure (60), The groups (A), (B), (C), represent additional HDCPC waveguide portions within the module each with its own optical I/Os through which radiation for (e.g. E.M.R 200 nm to about 2400 nm) bacteriological inactivation and/or dissolving, neutralizing, and/or deodorizing, and/or (optical) filtering, and/or spectral sensing (e.g. such as fluorescent events) to and/or from each individual HDCPC wave guide (HDCPC continues FIN) portion and/or extension providing a platform on which a plurality of light sources could be used (such as solid state diode lasers, flash lamps with wavelength from about 190 nm to about 3000 nm. The liquids or gasses inlet into the module is illustrated in (61) with a wide arrow above integral connection port to the edge of the adjacent HDCPC module (not shown). (61, a) represent ultrasound transient cavitation probe and (61, b,) illustrate a magnetron for the production of microwave energy therein (in the respective module or arrays of modules) (62) Represent a control and data acquisition unit capable of transmitting and receiving light from each individual HDCPC hollow waveguide portion therein (e.g. in the module enclosure). (63) Illustrate a bundle of individual wave-guides (not shown), wherein their common end termination (64), is shown for clarity as splitting into (a), (b), (c), (d), (e), (f), each representing an individual waveguide or optical fiber or tapered fibers assembly delivering optical energy to/and from said HDCPC waveguide portions within the module. The first, lower array of wave guides portions is represented by (65), (66), (67), the remaining HDCPC wave guides portions within the module are marked in groups of three from group (A), group (B), group (C), group (D), group (E), the groups are arranged and illustrated according to their respective positioning within the module. (68) Represent the lower quick coupling and integration shunts (e.g. a connecting secure ring) for connection to adjacent HDCPC (outlined) underneath at the bottom of the figure. (69) Illustrate the upper integration and connection shunt wherein, (69, a,) illustrate a pressure vessel module driver illustrating the novel methodological integration of devices according to the present invention with filtration systems of both molecular and particulate levels (70) represent the module's output (e.g. the liquids and/or gasses module outlet) marked with an arrow to the left, upper side of the module.

Figure 5:
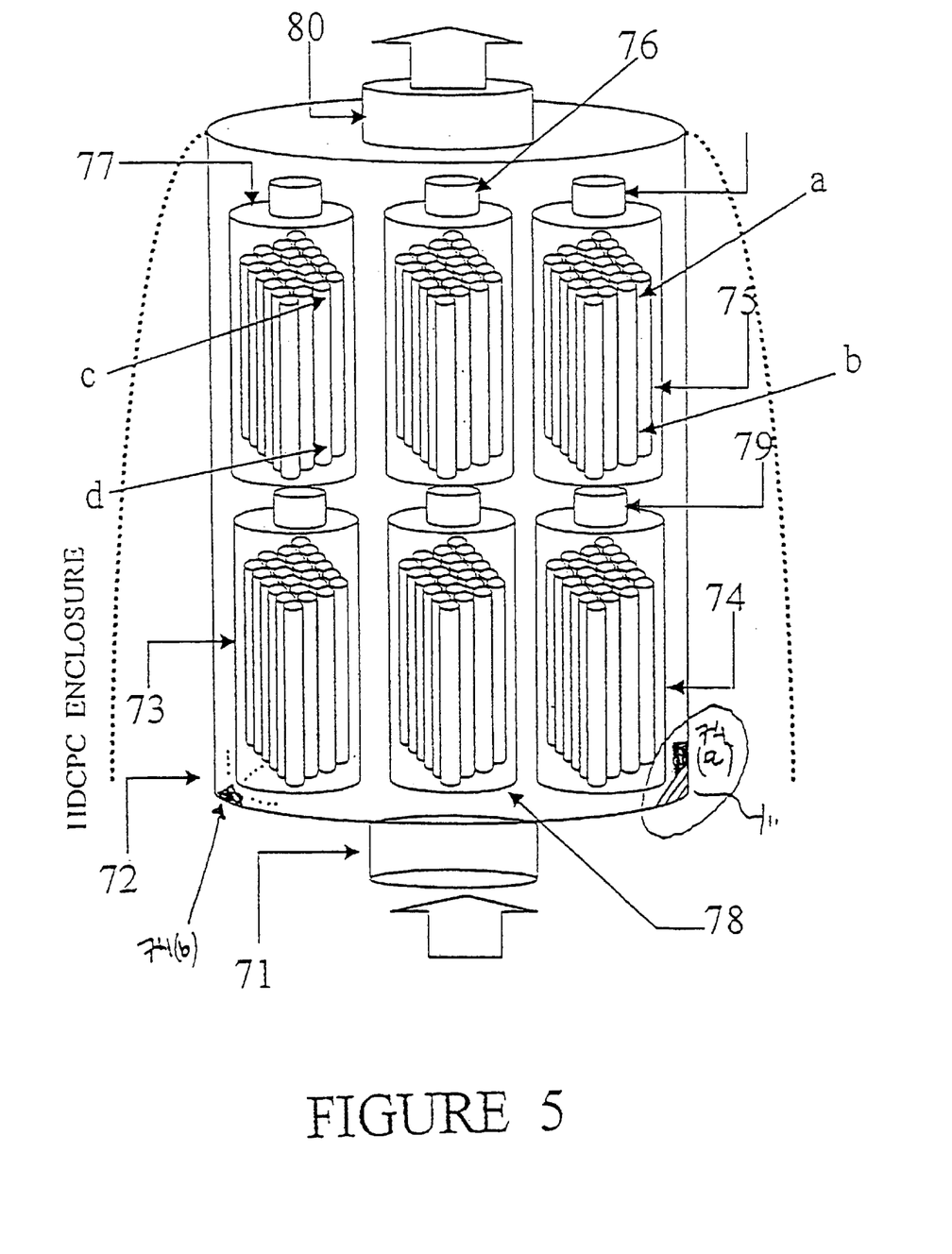
FIG. 5 is an isometric view of an array of modules positioned within a chamber-type larger module according to the present invention.

FIG. 5 illustrates an isometric view of an array of modules within a chamber type larger module according to the method of the present invention. An array of modules of the present invention is shown comprising (71) lower module inlet for liquids and/or gasses into the module (e.g. a module array within a module) (72). (73) Represent individual smaller module having the ability to stop particulate material above or below a predetermined threshold, as well as receive an optical feed (not shown). (74) Illustrates additional module positioned at the right side of the chamber type larger module. This module (74) is designated to stop particulate, organic and/or non-organic compounds on the molecular level above or bellow a predetermined threshold (74, a,) represent an ultrasound transient cavitation probe operating from about 26.5 kHz to about 180 kHz, (74, b,) represent a magnetron for the production of microwave energy therein (e.g. in the respective frame/module architecture (75) Represent a filtration module (molecular level) having illuminated membrane array illustrated as receiving two separate optical feed/takes marked as (a), and (b). (76) Illustrates a pressure-dependent tightening shunt/ring which acts as support means when pressure is rising or falling (into or out of the module). (77) Illustrates an array of illuminated filter tubes (particulate level) designated to stop particulate materials and suspended solids of a predetermined size threshold. (78) Represent a module containing an array of transparent thermo-set, and/or thermo-plastic elastic light conducting polymer (e.g. such as PDMs) combination wherein at least one waveguide portion within is coated with $SIO_2$ by plasma spattering and/or coated with additional layer of photocatalyst (e.g. such as $TIO_2$) on top, such as to form appropriate refractive index profile for enhanced transmission therein (throughout the module). (79) Illustrates connection between modules in the chamber in the form a pressure sensitive securing shunt and/or ring. (80) Represent the overall outlet, marked with an arrow (e.g. larger module output) for liquids and/or gasses, which have passed through the module with its internal arrays of smaller modules.

Figure 6:
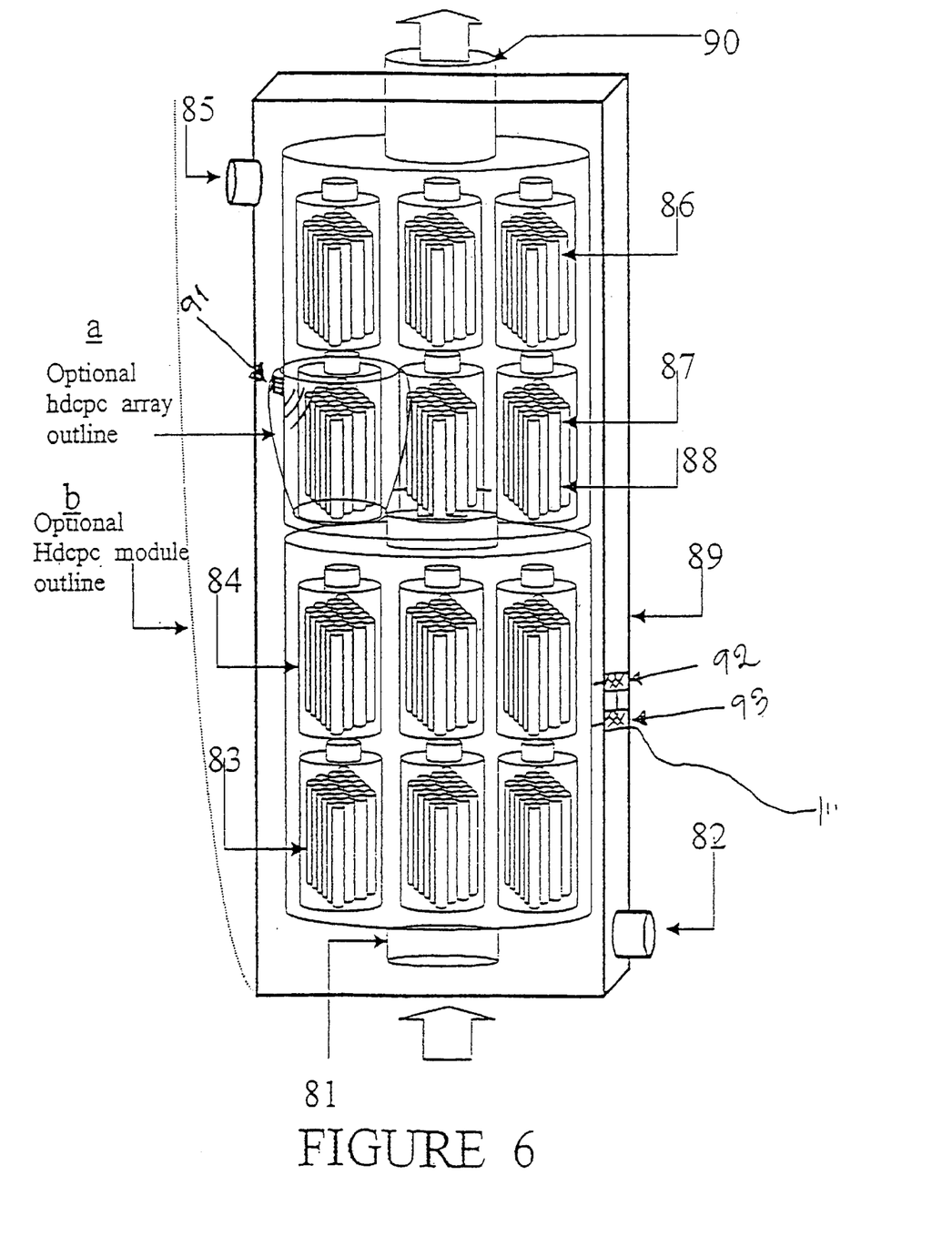
FIG. 6 is an isometric view of a disinfecting module according to the present invention.

FIG. 6 illustrates an isometric view of a disinfecting module according to the present invention. A disinfecting module according to the present invention is shown comprising: Liquid or gasses general inlet (water inlet is shown) indicated by the arrow is positioned for clarity parallel to the horizontal axis of the module (e.g. input is positioned in line with the modules length). (82) Represent additional water input positioned right at 90 degrees to the collective pointing layout of a plurality of plasma spattered or coated PDMs wave and/or liquid and/or gasses guides. Said pipes, each at a length from about (smaller) then 1 mm to about (bigger) then 100 meters. (83) Illustrates an individual wave and liquid (or gas) guide portion wherein said portion is part of an array of guides portions wherein said portion is dedicated for the introduction, mixing and melting oxygen (e.g. present in liquids or gasses) (84), (a), (b), represent optional embodiments to illustrate the integration of device s according to the method of the present invention with different filtration systems i.e. able to perform both molecular filtration level ((a), shown with a HDCPC shaped reactor or module enclosure, and/or particulate filtration levels (b)). (85) Illustrates side facing, (90 degrees), and general water outlet. (86) Represent a filtration module and waveguide integral to each of the respective member array. (87), (88) Illustrates additional module wherein two optical I/Os are shown for clarity, one for inputting light for the purpose of inactivation, disinfecting, neutralizing and/or deodorizing pollutants or noxious species. (89) Illustrates the frame of a larger square shaped module holding 12 enclosed modules (e.g. illumination and/or UV (e.g. PW or CW) irradiation modules (such as receiving external laser or flash lamps input from a remote and/or integrated radiation unit having high intensity source of light not shown). (90) illustrates the module general outlet (frame output) wherein the liquids and/or gasses output the system. (91) Illustrates an ultrasonic transient cavitation probe able to produce ultrasonic energy from about 27 kHz to about 218 kHz, preventing from colloidal deposits and/or hard water deposits from attaching to reactor (HDCPC) inner walls or surfaces (e.g. inner walls and surface of the waveguid portions (PDMs) included in each individual module. A frame i.e. a larger module could be used according to the method of the present invention wherein said frame is positioned before, and/or after, and/or during filtration processes comprising molecular filtration and particulate filtration such as exist in municipal waste water treatment, drinking water application and treatment of liquids and gasses in domestic industrial and agricultural applications, the present invention disclosed a novel methodology wherein a diversity of energies are launched resolved, and/or synchronized over predetermined time to ensure adequate delivery of disinfecting dose by the formation of high energy density zone (using HDCPC). (91), (93), illustrates the ability of the present invention to utilize any of its module as a pressure vessel, harness, use, integrate into or any combination thereof making use of hydraulically and pneumatically applied pressure (e.g. such as used in reverse osmosis, and other molecular and particulate threshold orientated filtration systems), the method of the present invention surpass limitation imposed by conventional systems i.e. in that devices according to the present invention could provide simultaneous filtration and/or irradiation inactivation of DNA and RNA replication sequences in noxious microorganisms, as well as triggering of photocatalyst for the production of free radicals and ultrasound transient cavitation for the prevention of colloidal deposits and hard water (liquids and/or gasses) deposits.

Figure 7:
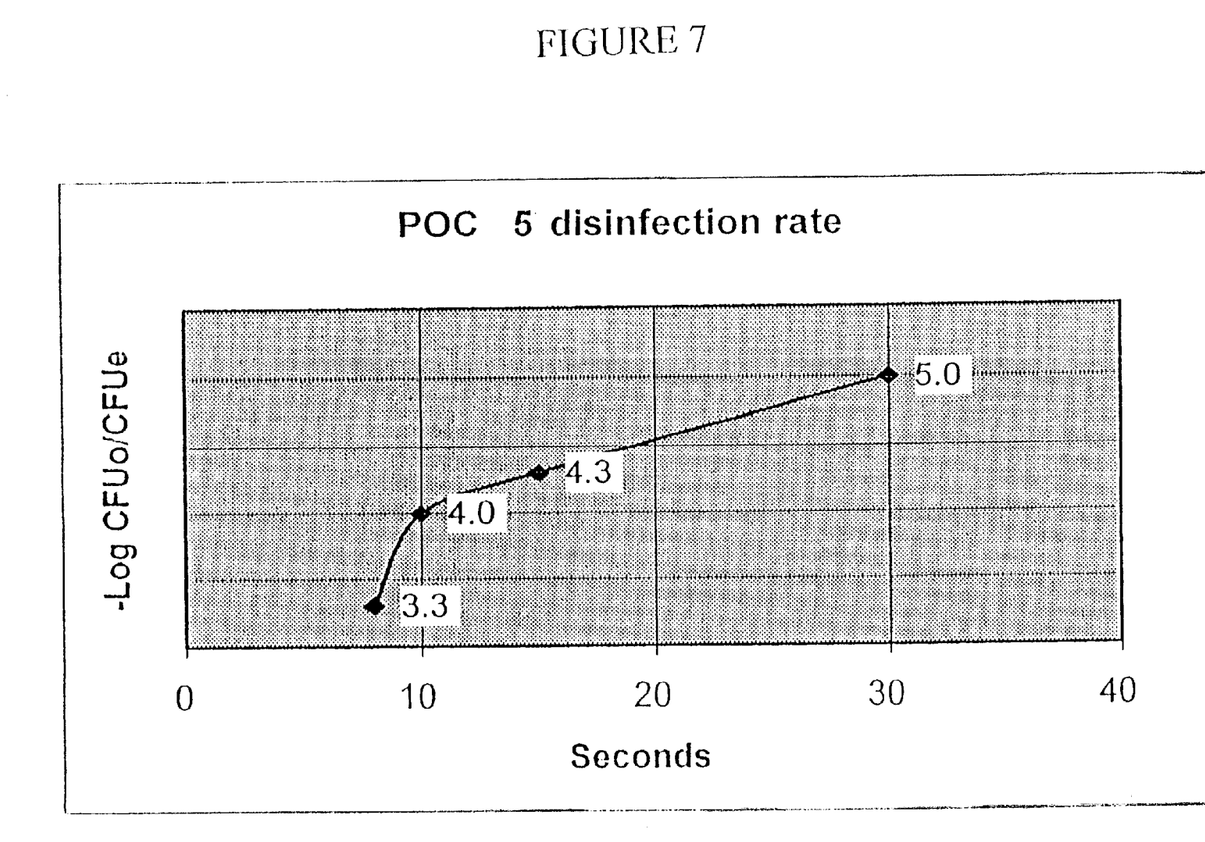
FIG. 7 is a graph showing experimental data obtained when the method of the present invention is implemented for treating, disinfecting, neutralizing and dissolving pollutants and noxious species.

FIG. 7 Illustrate a graph showing a proof of concept experimental data of the method of the present invention treating and disinfecting neutralizing and dissolving pollutants and noxious species wherein the numbers 0–40 represent time elapsed during irradiation and operation of the device according to the present invention, the title on the left indicate CFU count (in logs), the number highlighted in the graph body itself represent log inactivation from 3.3 around the 10 seconds mark and up to 5 log inactivation (99.9% inactivation, disinfecting), bacteria used in the experiment is *E. coli* wild type strain k 12. Laser at 266 nm wavelength, operating at 10 Hz, TIO2 photocatalyst was used plasmaspatterd on the walls of the titanium based reactor architecture, laser peak power 2.5–4 mJ respectively, ultrasound transient cavitation at 27 kHz, magnetron on, oxygen input active. Substantial CFU reduction was observed after 10–30 seconds.

Figure 8:
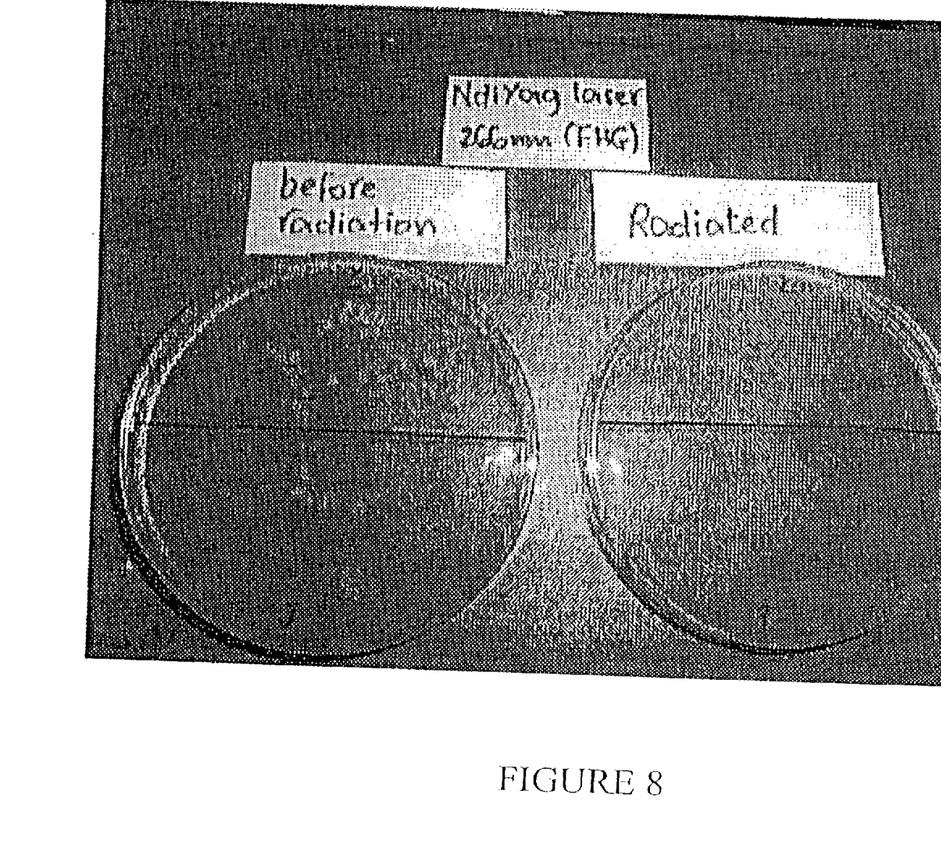
FIG. 8 is a photograph illustrating the efficiency of the method and device of the present invention.

FIG. 8, illustrates the efficiency of the method and devices of the present invention. The plate count on the left shows a CFU count (Colonies Forming Units) of Noxious species of E-Coli wild type, strain K 12, in agar and Cl at 0.9% suspension, which has not been exposed to the laser.

The plate on the right shows a total reduction of the E-Coli wild type, which clearly reaffirms the high efficiency of the non-chemical, non residual methodology of the present invetion. This experiment was performed, using an Antlantium Nd; YAG at 226 nm, using a pulse width of sub-microsecond time domain (ns) prompting 2nd order interactions.

What is claimed is:

1. A method of disinfecting and purifying a liquid or a gas, said method comprising the steps of:
    passing said liquid or gas through at least one reactor having a truncated compounded concentrator geometry; and
    simultaneously delivering and concentrating diversified electromagnetic and acoustic energies into a predetermined inner space of said reactor to form a high energy density zone in said reactor over a predetermined period of time.

2. A method according to claim 1, wherein the reactor is a compounded parabolic concentrator.

3. A method according to claim 2, wherein the liquid or gas is passed through an array of at least two said compounded parabolic concentrators connected serially.

4. A method according to claim 2, wherein the liquid or gas is passed through an array of at least two said compounded parabolic concentrators connected in parallel.

5. A method according to claim 1, wherein the reactor is a compounded ellipsoidal concentrator.

6. A method according to claim 1, wherein the electromagnetic energy is in any range of the electromagnetic spectrum.

7. A method according to claim 1, wherein the acoustic energy is of any suitable frequency.

8. A method according to claim 1, further comprising the step of positioning at least one source of the electromagnetic energy within the reactor.

9. A method according to claim 1, further comprising the step of positioning at least one source of the electromagnetic energy outside the reactor.

10. A method according to claim 1, further comprising the step of providing at least one source of the electromagnetic energy, which source is a laser.

11. A method according to claim 10, wherein the laser is a pulsed laser.

12. A method according to claim 1, further comprising the step of providing a radiation unit as a source of said electromagnetic energy, wherein the radiation unit, having a high intensity source of light, is a flash lamp having a high repetition rate of from about 1 Hz to about 50 kHz and a high peak power of from about 1 mJ to about 50 J.

13. A method according to claim 1, wherein an inner surface of the reactor is coated by a thin layer of photocatalyst.

14. A method according to claim 13, wherein the photocatalyst is $TiO_2$.

15. A method according to claim 1, wherein the electromagnetic energy is ultra-violet (UV) radiation having a wavelength of from about 200 nm to about 400 nm.

16. A method according to claim 15, wherein the UV radiation is pulsed.

17. A compounded concentrator reactor device for use in a method of disinfecting and purifying a liquid or a gas, wherein:
    said reactor device is a hollow truncated concentrator having a passage for the liquid or gas, said passage having a wider inlet and a narrower outlet; and
    said concentrator has a predetermined optical concentrating geometry capable of concentrating light to form a high density energy zone therein.

18. A device according claim 17, wherein the concentrator has an inner shape that has a compound parabolic or ellipsoidal concentrator geometry.

19. A device according to claim 17, wherein an inner wall of the concentrator has a coating comprising a photocatalyst layer.

20. A device according to claim 19, wherein the photocatalyst layer is made of $TiO_2$ (Titanium oxide).

21. A device according to claim 20, wherein the $TiO_2$ photocatalyst layer is plasma spattering coated to have a thickness of from about 0.8 micron to about 1000 micron.

22. A device according to claim 20, wherein said coating further comprises a substrate layer made of $SiO_2$ and having a thickness of from about 0.8 micron to about 1500 micron, said $TiO_2$ photocatalyst layer being coated on said substrate $SiO_2$ layer.

23. A device according to claim 19, wherein a refractive index of the coating is lower then a refractive index of the liquid or gas to flow in and be disinfected and purified by the reactor device.

24. A device according to claim 17, wherein
    an inner wall of the concentrator has a coating that has a plurality of grooves;
    said grooves are arranged in parallel or in a grid configuration; and
    a distance between two successive said grooves is less then a wavelength of light incident upon said grooves.

25. A device according to claim 17, wherein the reactor device is part of a reverse osmosis system or a filtration system.

26. A device according to claim 17, wherein an inner wall of the concentrator has a coating that is holographically grooved.

27. A device according to claim 17, further comprising a light source for generating light of a predetermined wavelength, said light source being optically coupled to said concentrator, wherein:
    an inner wall of the concentrator has a coating that has a plurality of grooves;
    said grooves are arranged in parallel or in a grid configuration; and
    a distance between two successive said grooves is less then said predetermined wavelength.

* * * * *